United States Patent
Raney et al.

(10) Patent No.: US 6,309,839 B1
(45) Date of Patent: Oct. 30, 2001

(54) SCREENING METHODS FOR COMPOUNDS THAT INHIBIT OR STIMULATE HELICASE ENZYME ACTIVITY

(75) Inventors: Kevin Raney; Patrick Morris; Regina Dennis, all of Little Rock, AR (US)

(73) Assignee: Board of Trustees of the University of Arkansas, Little Rock, AR (US)

(*) Notice: Subject to any disclaimer, the term of this patent is extended or adjusted under 35 U.S.C. 154(b) by 0 days.

(21) Appl. No.: 09/539,191

(22) Filed: Mar. 30, 2000

Related U.S. Application Data

(60) Provisional application No. 60/126,873, filed on Mar. 30, 1999.

(51) Int. Cl.[7] .................. C12Q 1/68; G01N 33/53; C12P 19/34; C12N 9/00; C07H 21/02
(52) U.S. Cl. ............... 435/6; 435/7.1; 435/7.72; 435/7.8; 435/91.1; 435/183; 536/23.1
(58) Field of Search ............... 435/5, 6, 7.72, 435/7.1, 7.8, 7.2, 91.1, 183, 188; 536/23.1, 24.1; 204/450

(56) References Cited

PUBLICATIONS

Ahnert et al. J. Biol. Chem. vol. 272, No. 51, pp. 32,267–32, 273, 1997.*
Young et al. J. Mol. Biol., vol. 235, No. 1447–1558, 1994.*
Yong et al. Chem. Res. Toxicol. vol. 9, pp. 179–187, 1996.*
Hacker et al. Biochem. vol. 36, pp. 14,080–14,087, 1997.*
Raney et al. Proc. Natl. Acad. Sci., USA, vol. 91, pp. 6644–6648, 1994.*

* cited by examiner

*Primary Examiner*—Andrew Wang
*Assistant Examiner*—Jane Zara
(74) *Attorney, Agent, or Firm*—Benjamin Aaron Adler

(57) ABSTRACT

The gp41 and Dda helicases were found to significantly enhance the dissociation rate of streptavidin from biotin-labeled oligonucleotides in an ATP dependent reaction, demonstrating that these enzymes are capable of imparting a significant force on a molecule blocking their path. The present invention describes an assay for studying enzymatic activity of a helicase using the rate of dissociation of streptavidin from biotinylated oligonucleotides.

12 Claims, 9 Drawing Sheets

SEQUENCE LISTING

<160> NUMBER OF SEQ ID NOS: 6

<210> SEQ ID NO 1
<211> LENGTH: 60
<212> TYPE: DNA
<213> ORGANISM: artificial sequence
<220> FEATURE:
<222> LOCATION: 2
<223> OTHER INFORMATION: 5'-bio-60-mer oligonucleotide sequence used for
      streptavidin displacement experiments;
      n = unknown at nucleotide 2 is biotinylated

<400> SEQUENCE: 1
gnacgtattc aagatacctc gtactctgta ctgactgcga tccgactgtc         50
ctgcatgatg                                                     60

<210> SEQ ID NO 2
<211> LENGTH: 61
<212> TYPE: DNA
<213> ORGANISM: artificial sequence
<220> FEATURE:
<222> LOCATION: 60
<223> OTHER INFORMATION: 3'-bio-61-mer oligonucleotide sequence used for
      streptavidin displacement experiments;
      n = unknown at nucleotide 60 is biotinylated

<400> SEQUENCE: 2
taacgtattc aagatacctc gtactctgta ctgactgcga tccgacgtcc         50
tgcatgatgn t                                                   61

<210> SEQ ID NO 3
<211> LENGTH: 30
<212> TYPE: DNA
<213> ORGANISM: artificial sequence
<220> FEATURE:
<222> LOCATION: 29
<223> OTHER INFORMATION: 3'-bio-30-mer oligonucleotide sequence
      used for streptavidin displacement experiments;
      n = unknown at nucleotide 29 is biotinylated

<400> SEQUENCE: 3
ctgactgcga tccgactgtc ctgcatgang                               30

<210> SEQ ID NO 4
<211> LENGTH: 21
<212> TYPE: DNA
<213> ORGANISM: artificial sequence
<220> FEATURE:
<222> LOCATION: 20
<223> OTHER INFORMATION: 3'-bio-21-mer oligonucleotide sequence used for
      streptavidin displacement experiments;
      n = unknown at nucleotide 20 is biotinylated

<400> SEQUENCE: 4
atcctactgt cctgcatgan g                                        21

<210> SEQ ID NO 5
<211> LENGTH: 16
<212> TYPE: DNA
<213> ORGANISM: artificial sequence
<220> FEATURE:
<222> LOCATION: 15
<223> OTHER INFORMATION: 3'-bio-16-mer oligonucleotide sequence used for
      streptavidin displacement experiments;
      n = unknown at nucleotide 15 is biotinylated -continued

```
<400> SEQUENCE: 5
tcctgcatga tgagnt                                                       16

<210> SEQ ID NO 6
<211> LENGTH: 11
<212> TYPE: DNA
<213> ORGANISM: artificial sequence
<220> FEATURE:
<222> LOCATION: 10
<223> OTHER INFORMATION: 3'-bio-11-mer oligonucleotide sequence used for
      streptavidin displacement experiments;
      n = unknown at nucleotide 10 is biotinylated

<400> SEQUENCE: 6
tgcatgatgn t                                                            11
```

SCREENING METHODS FOR COMPOUNDS THAT INHIBIT OR STIMULATE HELICASE ENZYME ACTIVITY

CROSS-REFERENCE TO RELATED APPLICATION

This non-provisional patent application claims benefit of provisional patent application U.S. Ser. No. 60/126,873, filed Mar. 30, 1999, now abandoned.

BACKGROUND OF THE INVENTION

1. Field of the Invention

The present invention relates generally to the field of molecular biology. More specifically, the present invention relates to helicases and methods of screening for compounds that inhibit or stimulate helicase enzyme activity.

DESCRIPTION OF THE RELATED ART

DNA helicases are molecular motors that transduce the energy obtained from hydrolysis of nucleotide triphosphates (NTPs) to perform the mechanical work of unwinding double-stranded (ds) DNA (1,2,3,4,5). These enzymes are ubiquitous and necessary for most aspects of nucleic acid metabolism, including replication, repair, and recombination. Several disease states have recently been associated with defective helicases, such as Bloom's syndrome (6) and xerodoma pigmentosum (7). However, the biochemical mechanism(s) of helicases are largely unknown.

The E. coli Rep helicase has been closely studied and a mechanism has been proposed for this dimeric enzyme (2, 5). One subunit of Rep is proposed to bind ssDNA while the other binds and unwinds dsDNA in a cyclic process coordinated by binding and hydrolysis of ATP. The preferential affinity of one subunit of the dimer for dsDNA over ssDNA at a ds/ss DNA junction is proposed to drive translocation of the enzyme via a "rolling" or "subunit switching" mechanism. This mechanism predicts that little or no directional bias occurs during translocation on ssDNA substrates. In contrast, others have proposed that some helicases translocate unidirectionally on ssDNA, and that such activity is important to the overall mechanism of dsDNA unwinding (8). A model for translocation by the E. coli transcription termination protein Rho has been provided that includes a directionally biased random walk along RNA (9). Evidence has been provided suggesting that the bacteriophage helicases gp41and Dda translocate unidirectionally on ssDNA (10, 11).

gp41 subunits can oligomerize into a hexamer in the presence of ATPor GTP(12), and serves as the replicative helicase of bacteriophage T4. Investigators using electron microscopy have determined that some hexameric helicases bind to DNA by encircling it, such that the DNA passes through the central channel of the hexamer (reviewed in 3). Results from biochemical experiments (13) may be interpreted as being consistent with similar DNA binding by gp41. The present invention provides additional evidence based upon biochemical studies that suggests that gp41 encircles ssDNA.

One outstanding question regarding helicase function deals with the direction and mechanism of translocation on ssDNA. Studies of another molecular motor protein, the $F_1$-ATPase, may provide clues towards answering this question. The hexameric form of helicases with DNA passing through the central channel is somewhat analogous to the $F_1$-ATPase, which consists of a hexamer of $\alpha 3\_\beta$ subunits encircling a $\gamma$ subunit (14). Rotation of the $\gamma$ subunit within the cylinder of the hexamer has been directly observed in the presence of ATP (15). Recently, the dTTPase activity of the hexameric gene 4 helicase from bacteriophage T7 was found to resemble the mechanism of the $F_1$-ATPase, in which three of the six potential nucleotide binding sites on the hexamer are catalytic sites and three are noncatalytic sites (16). A rotational movement of the gene 4 hexamer around the ssDNA was proposed to result in unidirectional translocation and unwinding of duplex DNA.

Others have recently proposed an inch-worm mechanism involving unidirectional translocation on RNA or ssDNA based upon the crystal structure of the non-structural protein 3 (NS3) helicase from the hepatitis C virus (17). If helicases translocate unidirectionally on ssDNA, the enzyme may produce a force in the direction of translocation. The effect of force on biochemical kinetics has recently received much attention (18). Technical innovations with atomic force microscopy (AFM), optical tweezers, and other methods have allowed direct measurement of the forces involved in binding of a ligand to its receptor as well as the forces generated by a translocating enzyme (19). The invention described herein provides evidence for production of force by DNA helicases, which suggests that the helicase has a strong directional bias on ssDNA. When challenged with biotinylated-oligonucleotide substrates to which streptavidin has been bound, the gp41 and Dda helicases can rapidly displace the streptavidin, suggesting that these enzymes impart a strong unidirectional force on the streptavidin.

The prior art is deficient in methods of screening for compounds that inhibit or stimulate helicase enzyme activity that do not rely upon a double-stranded DNA template. The present invention fulfills this longstanding need and desire in the art.

SUMMARY OF THE INVENTION

The present invention describes a new assay for studying enzymatic activity of gp41, Dda, HCV NS3, SV40 T antigen, and any other helicase on single-stranded DNA using the rate of dissociation of streptavidin from various biotinylated oligonucleotides in the presence of a helicase. gp41, Dda HCV NS3, and SV40 T antigen were found to significantly enhance the dissociation rate of streptavidin from biotin-labeled oligonucleotides in an ATP dependent reaction, thereby indicating that these enzymes are capable of imparting a significant amount of force on a molecule blocking their path.

In one embodiment, the present invention provides for a method of screening for compounds that inhibit or stimulate helicase enzyme activity, comprising the steps of: (a) combining under appropriate conditions: (i) a helicase enzyme; and (ii) a biotinylated oligonucleotide bound to streptavidin (SA-B-oligo), thereby producing helicase-associated SA-B-oligo; (b) contacting a sample of the helicase-associated SA-B-oligo with a compound, thereby producing a compound-treated helicase-associated SA-B-oligo sample; and (c) measuring the amount of dissociation of the biotinylated oligonucleotide from streptavidin in the compound-treated helicase-associated SA-B-oligo sample and an untreated helicase-associated SA-B-oligo sample. Less dissociation of the biotinylated oligonucleotide from the streptavidin in the compound-treated helicase-associated SA-B-oligo sample than in the untreated helicase-associated SA-B-oligo sample indicates that the compound inhibits the helicase enzyme activity. Greater dissociation of the biotinylated oligonucleotide from the streptavidin in the compound-treated helicase-associated SA-B-oligo sample than in the untreated helicase-associated SA-B-oligo sample indicates that the compound stimulates the helicase enzyme activity.

In yet another embodiment of the present invention, there is provided a method of releasing a streptavidin-captured, biotinylated oligonucleotide, comprising the steps of: (a) contacting a streptavidin-captured biotinylated oligonucleotide with a helicase; and (b) collecting the biotinylated oligonucleotide released from the streptavidin.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1 shows the removal of streptavidin from a 60 mer biotin labeled oligonucleotide catalyzed by the NS3 helicase.

FIG. 3 shows the helicase mediated displacement of streptavidin from a biotinylated oligonucleotide.

FIG. 6 shows the rate of streptavidin displacement from $^{3'}$-biotinylated oligonucleotides of varying lengths.

DETAILED DESCRIPTION OF THE INVENTION

Figure 1A:
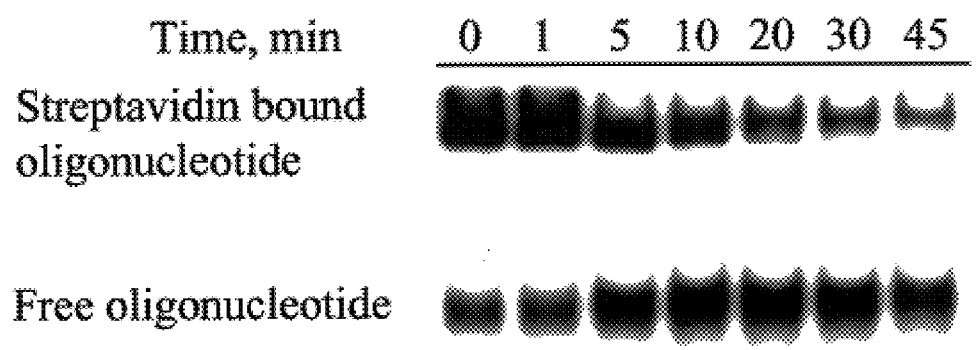
FIG. 1A shows the separation of streptavidin bound oligonucleotide from free oligonucleotide using native polyacrylamide gel electrophoresis.

Helicases are enzymes which use energy derived from nucleotide triphosphate hydrolysis to unwind dsDNA, a process vital to virtually every phase of DNA metabolism. The helicases used in the study described herein, gp41 and Dda, are from the bacteriophage T4. gp41 is the replicative helicase and has been shown to form a hexamer in the presence of ATP.

The present invention further describes a new assay, using the rate of dissociation of streptavidin from various biotinylated oligonucleotides in the presence of helicase, for studying enzymatic activity of gp41 and Dda on single-stranded DNA.

Using the above-mentioned assay, gp41, Dda, NS3, and SV40 T antigen were found to significantly enhance the dissociation rate of streptavidin from biotin-labeled oligonucleotides in an ATP dependent reaction. Helicase-catalyzed dissociation of streptavidin from the 3'-end of a biotin-labeled 62-mer oligonucleotide occurred with a first order rate of 0.17 min.$^{-1}$, which is over 500-fold faster than the spontaneous dissociation rate of biotin from streptavidin. Dda activity leads to even faster displacement of streptavidin from the 3' end of the 62-mer, with a first order rate of 7.9 s$^{-1}$. This is more than one million-fold greater than the spontaneous dissociation rate. There was no enhancement of streptavidin dissociation from the 5'-biotin-labeled oligonucleotide by either helicase.

The fact that each helicase was capable of dislodging streptavidin from the 3'-biotin label suggests that these enzymes are capable of imparting a significant amount of force on a molecule blocking their path. The difference in displacement between the 5' and 3'-ends of the oligonucleotide is also consistent with a 5'-to-3' translocation directional bias for each helicase on ssDNA.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984). Therefore, if appearing herein, the following terms shall have the definitions set out below.

As used herein, the term "cDNA" shall refer to the DNA copy of the mRNA transcript of a gene.

As used herein, the term "derived amino acid sequence" shall mean the amino acid sequence determined by reading the triplet sequence of nucleotide bases in the cDNA.

As used herein the term "screening a library" shall refer to the process of using a labeled probe to check whether, under the appropriate conditions, there is a sequence complementary to the probe present in a particular DNA library. In addition, "screening a library" could be performed by PCR.

As used herein, the term "PCR" refers to the polymerase chain reaction that is the subject of U.S. Pat. Nos. 4,683,195 and 4,683,202 to Mullis, as well as other improvements now known in the art.

The amino acid described herein are preferred to be in the "L" isomeric form. However, residues in the "D" isomeric form can be substituted for any L-amino acid residue, as long as the desired functional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, *J Biol. Chem.*, 243:3552–59 (1969), abbreviations for amino acid residues are known in the art.

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment. A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains (consensus sequences) responsible for the binding of RNA polymerase. Eukaryotic promoters often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control of" or "operably linked to" transcriptional and translational control sequences in a cell when RNA polymerase transcribes the coding sequence into mRNA, which is then translated into the protein encoded by the coding sequence.

A "signal sequence" can be included near the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide", as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and the method used. For example, for diagnostic applications, depending on the complexity of the target sequence, the oligonucleotide primer typically contains 15–25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementary with the sequence to hybridize therewith and thereby form the template for the synthesis of the extension product.

As used herein, the terms "restriction endonucleases" and "restriction enzymes" refer to enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90% or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

The labels most commonly employed for these studies are radioactive elements, enzymes, chemicals which fluoresce when exposed to ultraviolet light, and others. A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate.

Proteins can also be labeled with a radioactive element or with an enzyme. The radioactive label can be detected by any of the currently available counting procedures. The preferred isotope may be selected from $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090, 3,850,752, and 4,016,043 are referred to by way of example for their disclosure of alternate labeling material and methods.

Methods which are well known to those skilled in the art can be used to construct expression vectors containing appropriate transcriptional and translational control signals. See for example, the techniques described in Sambrook et al., 1989, *Molecular Cloning: A Laboratory Manual* (2nd Ed.), Cold Spring Harbor Press, N.Y. A gene and its transcription control sequences are defined as being "operably linked" if the transcription control sequences effectively control the transcription of the gene. Vectors of the invention include, but are not limited to, plasmid vectors and viral vectors.

Abbreviations used herein are as follows: ssDNA, single-stranded DNA; dsDNA, double-stranded DNA; SDS, sodium dodecyl sulfate; PK/LDH, phosphoenol pyruvate kinase/lactate dehydrogenase; DSP, dithiosuccinimidyl propionate.

As used herein, gp41 refers to the product encoded by the T4 41 gene.

The current invention is directed towards a method of screening for helicase-specific compounds (as opposed to compounds that may also bind non-specifically to the DNA or RNA template) that inhibit or stimulate helicase enzyme activity.

The present invention provides for a method of screening for compounds that inhibit or stimulate helicase enzyme activity, comprising the steps of: (a) combining under appropriate conditions: (i) a helicase enzyme; and (ii) a biotinylated oligonucleotide bound to streptavidin (SA-B-oligo), thereby producing helicase-associated SA-B-oligo; (b) contacting a sample of the helicase-associated SA-B-oligo with a compound, thereby producing a compound-treated helicase-associated SA-B-oligo sample and an untreated helicase-associated SA-B-oligo sample; and (c) measuring the amount of dissociation of the biotinylated oligonucleotide from streptavidin in the compound-treated helicase-associated SA-B-oligo sample and the untreated helicase-associated SA-B-oligo sample, wherein less dissociation of the biotinylated oligonucleotide from the streptavidin in the compound-treated helicase-associated SA-B-oligo sample than in the untreated helicase-associated SA-B-oligo sample is indicative of a compound that inhibits the helicase enzyme activity, wherein greater dissociation of the biotinylated oligonucleotide from the streptavidin in the compound-treated helicase-associated SA-B-oligo sample than in the untreated helicase-associated SA-B-oligo sample is indicative of a compound that stimulates the helicase enzyme activity.

Preferably, the streptavidin is in solution or is bound to a solid support. The streptavidin may also be mutated to alter it's dissociation constant from biotin. Representative sites on the oligonucleotide for biotinylation are at it's 3' end or at an internal nucleotide. Generally, the oligonucleotide is single-stranded. The source of the helicase may be viral, prokaryotic, eukaryotic, and bacteriophage. Additionally, the helicase may be defective, and may result in a disease such as xerodoma pigmentosum, or Bloom's syndrome. Further, the biotinylated oligonucleotide may also b e labeled with a non-biotin label, such as a radionucleotide, to allow for detection and quantitation of the dissociation of the biotinylated oligonucleotide from the streptavidin.

The present invention is further directed towards a method of of screening for compounds that inhibit or stimulate helicase enzyme activity, comprising the steps of: releasing a streptavidin-captured, biotinylated oligonucleotide, comprising the steps of: (a) contacting a streptavidin-captured biotinylated oligonucleotide with a helicase; and (b) collecting the biotinylated oligonucleotide released from the streptavidin. Preferably, the streptavidin is selected from the group consisting of in solution and bound to a solid support.

The present invention is further directed towards a method of screening for compounds that inhibit or stimulate helicase enzyme activity, comprising the steps of: (a) combining under appropriate conditions: (i) a helicase enzyme; and (ii) a single-stranded DNA or RNA oligonucleotide to which has been attached a small molecule, herein called the labeled oligonucleotide. A protein that binds to the small molecule is added to the oligonucleotide to create a protein-small molecule-oligonucleotide complex; (b) contacting a sample of said helicase-associated labeled oligonucleotide with a compound, thereby producing a compound-treated helicase-associated small-molecule-protein-oligonucleotide sample; and (c) measuring the amount of dissociation of labeled oligonucleotide from the protein in said compound-treated helicase-associated labeled oligonucleotide. Representative small molecules which can be used to prepare labeled oligonucleotides and the proteins that they bind are listed:

| small molecule | protein that binds to labeled oligonucleotide |
|---|---|
| biotin and its derivatives | streptavidin, avidin, monoclonal antibody to biotin |
| bromouridine | monoclonal antibody to bromouridine |
| digoxigenin | monoclonal antibody to deoxigenin |
| cholesterol | monoclonal antibody to cholesterol, cholesterol receptor |
| acridine | monoclonal antibody to acridine |

The following examples are given for the purpose of illustrating various embodiments of the invention and are not meant to limit the present invention in any fashion.

EXAMPLE 1

Materials

The following compounds were used herein and were obtained from the indicated sources: Streptavidin, PKILDH (Sigma); ATP, biotin and acrylamide (Fisher); radioactive ATP (New England Nuclear); DSP (Pierce); T4 polynucleotide kinase and M13 ssDNA (New England Biolabs); and SYBR Green II nucleic acid stain (Molecular Probes). Oligonucleotides were synthesized by Operon using either the Bio-TEG biotin label, in which the biotin was placed at either the 5'- or 3'- end, or the Biotin-On biotin label, in which the biotin label was placed internally. Dda helicase was overexpressed and purified as described (11, 20).

EXAMPLE 2 gp41 purification gp41 was expressed in E. coli strain OR1265/pDH518 by temperature induction at 42° C. for 3 hrs (21). Cells were suspended in lysis buffer (0.2 mg/mL lysozyme, 0.5 mM PMSF, 50 mM Tris acetate (pH 7.4), 1 mM EDTA), sonicated, and centrifuged at 16,000 rpm for 30 min. The pellet was then re-suspended in extraction buffer (22) (20 mM Tris acetate (pH 7.4), 10 mM $MgCl_2$, 1.0 mM DTT, 2.0 M urea, 10% sucrose). Barry and Alberts (22) reported that utilization of urea in the buffer facilitates solubilization of gp41 and results in protein with the same or higher specific activity as gp41 prepared by alternative protocols (21). After 1 hr at 4° C., this solution was centrifuged at 40,000 rpm for 2 hrs in a Beckman Ti70 rotor, leaving the protein in the supernatant. gp41 was then applied to a macro-prep high Q strong anion exchange resin (BioRad) equilibrated with extraction buffer, and eluted with a linear NaCl gradient from 0 to 500 mM. Fractions containing gp41, which eluted at 200–250 mM NaCl, were identified by SDS-PAGE, pooled, and dialyzed into extraction buffer. gp41 was then applied to a ssDNA-cellulose column (Amersham Pharmacia Biotech), eluted with a linear NaCl gradient from 0 to 2.0 M, and fractions were analyzed by SDS-PAGE . gp41 eluted at 80–380 mM NaCl. Protein was dialyzed into MOPS extraction buffer (25 mM MOPS (pH 6.7), 1.0 M urea, 10 mM $MgCl_2$, 1 mM DTT, 5% glycerol) and applied to a macro-prep high S strong cation exchange resin (BioRad). Protein was eluted with a linear gradient from 0 to 500 mM NaCl, with gp41 eluting at 315–450 mM NaCl, and fractions were analyzed by SDS-PAGE. At this point, the protein appeared to be>95% pure. Half of the purified protein was dialyzed into a buffer of 25 mM Hepes (pH 8.0), 1.0 mM EDTA, 20% glycerol, 50 mM KOAc, 5 mM BME. The other half was dialyzed into the same buffer without BME and this stock was used for experiments involving DSP cross-linking. Aliquots of protein were stored at –80° C.

EXAMPLE 3

Oligonucleotide purification and labeling

Oligonucleotides were purified by denaturing 20% polyacrylamide gel electrophoresis and electroeluted from the gel using an Elutrap apparatus (Schleicher & Schuell). DNA was desalted using a Water's Sep-Pak column, and dried via Speed-Vac (Savant). Oligos were re-suspended in 10 mM Hepes (pH 7.5) and 1 mM EDTA, and quantitated by their $A_{260}$ after dilution in 0.2 M KOH using calculated extinction coefficients. Oligonucleotides were 5'-radiolabeled with T4 polynucleotide kinase at 37° C. for 1 hr. The kinase was inactivated by heating to 85° C. for 10 min. Unincorporated [$\gamma^{32}P$]-ATP was removed by twice passing the labeled oligos through a Sephadex G-25 spin column. Oligonucleotide sequences for the streptavidin displacement experiments were as follows (with X signifying a biotin label):

5'-bio-60-mer: 5'-GXACGTATTC AAGATACCTC GTACTCTGTA CTGACTGCGA TCCGACTGTC CTGCATGATG-3' (SEQ ID NO. 1);

3 '-bio-61-mer: 5'-TAACGTATTC AAGATACCTC GTACTCTGTA CTGACTGCGA TCCGACGTCC TGCATGATGX T-3' (SEQ ID NO. 2);

3'-bio-30-mer: 5'-CTGACTGCGA TCCGACTGTC CTGCATGAXG-3' (SEQ ID NO. 3);

3'-bio-21-mer: 5'-ATCCGACTGT CCTGCATGAX G-3' (SEQ ID NO. 4);

3'-bio-16-mer: 5'-TCCTGCATGA TGAGXT-3' (SEQ ID NO. 5);

3'-bio-11-mer: 5'-TGCATGATGX T-3' (SEQ ID NO.6).

EXAMPLE 4

Streptavidin displacement experiment

5'-radiolabeled oligos with biotin on either their 5' or 3'-end were utilized in this experiment. 10 nM oligonucleotide was incubated in helicase reaction buffer (25 mM Hepes (pH 7.5), 12.5 mM Mg(OAc)$_2$, 150 mM KOAc, 4 mM PEP, 1 mM BME, 0.1 mg/mL BSA), along with 5 mM ATP and 300 nM streptavidin at 37° C. for 2–3 min. PK and LDH, 10.8 units/mL and 16.7 units/mL, respectively, and 6 $\mu$M free biotin trap were added. The reaction was initiated upon addition of helicase at the concentrations described in the figure legends. At various times, 10 $\mu$L aliquots were removed and mixed with 10 $\mu$L of helicase quench buffer (0.6% SDS, 200 mM EDTA (pH 8.0), 10 $\mu$M poly dT). Gel loading buffer (0.1% xylene cyanol, 0.1% bromophenol blue, 10% glycerol) was added to each sample, followed by electrophoretic analysis on a 15% native polyacrylamide gel. The fraction of free oligonucleotide and streptavidin-bound oligonucleotide was determined for each sample using the Molecular Dynamics Phosphorimager. Oligo length for each experiment ranged from 11 to 62 nucleotides, and gp41 concentration varied from 250 nM to 4 $\mu$M as described in the figure legends.

For the Dda helicase, a Kintek rapid chemical quench-flow instrument (KINTEK, Inc., State College, Pa.) was used to measure very fast dissociation of streptavidin from biotin-labeled oligonucleotides. The reaction was performed using two different protocols. In the first method, Dda in helicase reaction buffer was rapidly mixed with the biotin-labeled oligonucleotide (10 nM after mixing) and ATP (5 mM after mixing). The reaction mixture was incubated for varying times, then stopped by rapidly mixing with helicase quench buffer. In the second method, Dda in helicase assay buffer was preincubated with the biotin labeled oligonucleotide followed by initiation of the reaction by mixing with ATP. The concentration of Dda for each experiment is listed in the figure legends. The receiving vial for each sample contained poly dT (5 $\mu$M after addition of the reaction mixture) in order to prevent a gel shift of the biotin-labeled oligonucleotide due to helicase binding. An aliquot (25 $\mu$L) of each sample was mixed with non-denaturing gel loading buffer (4 $\mu$L), followed by analysis of samples by gel electrophoresis, visualization using a phosphorimager, and quantitation using Imagequant software (Molecular Dynamics).

EXAMPLE 5

The gp41 hexamer binds ssDNA by encircling the DNA strand

Studies using electron microscopy, as with gene 4 protein and E. coli RuvB, and biochemical technique, as with SV40 T antigen, have revealed that hexameric helicases can bind to their DNA substrates by encircling them (23, 24, 25). gp41 is a hexamer with dimensions similar to the gene 4 helicase (12). Previous work using biotinylated oligonucleotides bound with streptavidin suggested that one strand of DNA passes through the channel of gp41 during DNA unwinding (13). To further investigate this possibility, protein cross-linking experiments have been utilized to analyze the binding topology of the hexamer in a manner similar to that described for the gene 4 helicase (23). gp41 can be readily cross-linked as a hexamer by the chemical cross-linker dithiosuccinimidyl propionate (DSP) in the presence of nucleotide triphosphates ATP or GTP, as well as the non-hydrolyzable analogs, ATP-$\gamma$-S and GTP-$\gamma$-S (12). Chemical cross-linking of gp41 has been used in conjuction with electrophoretic gel mobility shift analyses of ssDNA to investigate whether gp41 encircles the DNA.

Gp41 hexamer cross-linking was examined in the presence of linear ssDNA. In the absence of DSP, gp41 binding retards DNA migration through the gel. When the non-crosslinked gp41 is subjected to denaturing conditions, the DNA shift disappears. In the presence of DSP, gp41 again shifts DNA, unless it is subjected to denaturing conditions, in which case the shift disappears. This result indicates that DSP does not crosslink gp41 to the DNA.

Gp41 hexamer cross-linking was also examined in the presence of M13 circular ssDNA. In the absence of DSP, gp41 hexamer binding causes DNA to be shifted, and as with the oligonucleotide, this shift disappears with the introduction of denaturing conditions. In the presence of DSP, the DNA band is shifted regardless of the presence or absence of denaturing conditions. These results can be interpreted as hexameric gp41 binding ssDNA by encircling the DNA strand. In the absence of DSP, heat and SDS treatment causes the hexamer to dissociate from both linear and circular ssDNA, due to disruption of both DNA-protein binding and protein-protein interactions between hexameric subunits. When gp41 hexamer is treated with DSP, the protein subunits are linked by covalent bonds which are not broken by denaturation, although DNA-protein binding is lost as shown with the oligonucleotide data not shown. Denaturing treatment causes the cross-linked hexamer to dissociate from linear ssDNA, because gp41 binding to DNA is disrupted and the hexamer can slide off the end o f the DNA strand. The crosslinked hexamer will not, however, dissociate from circular ssDNA under denaturing conditions. Binding between gp41 and DNA is disrupted, but there is no free DNA end for the cross-linked hexamer to slide off of, and the DNA band remains shifted on the gel.

Figure 1B:
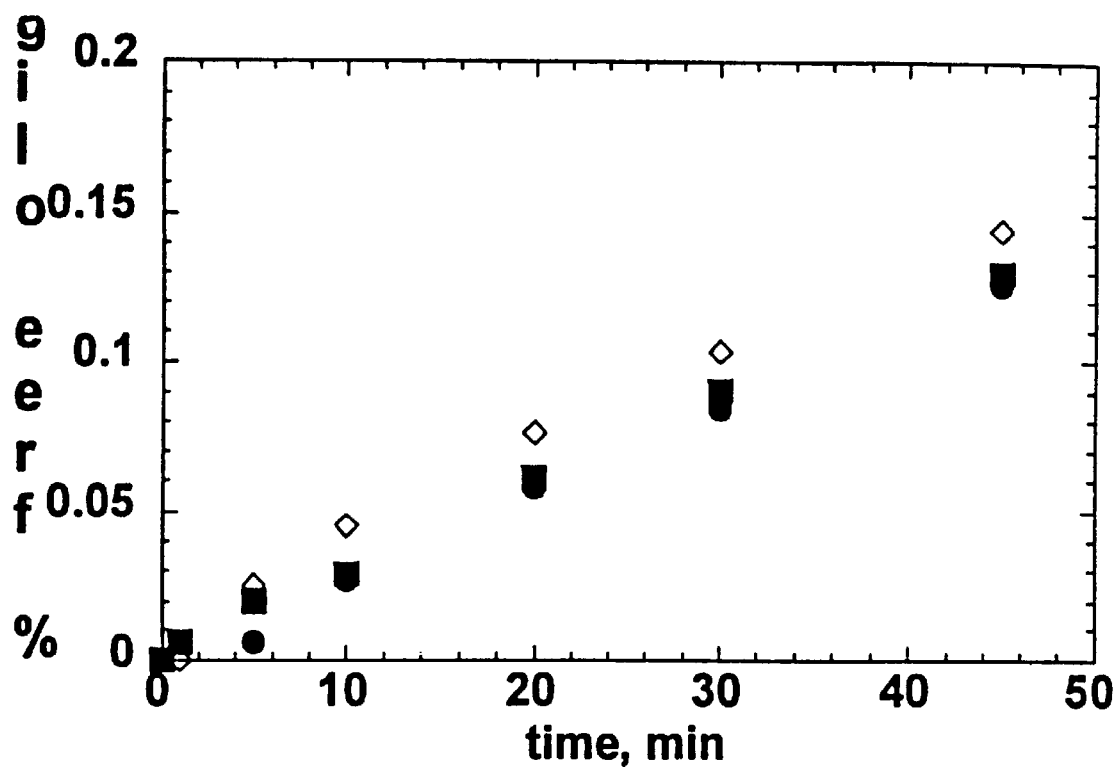
FIG. 1B shows results plotted showing the linearity of the reaction over time, when the reaction is conducted under the conditions described here: NS3 was 10 nM, oligonucleotide was 100 nM.
Figure 2:
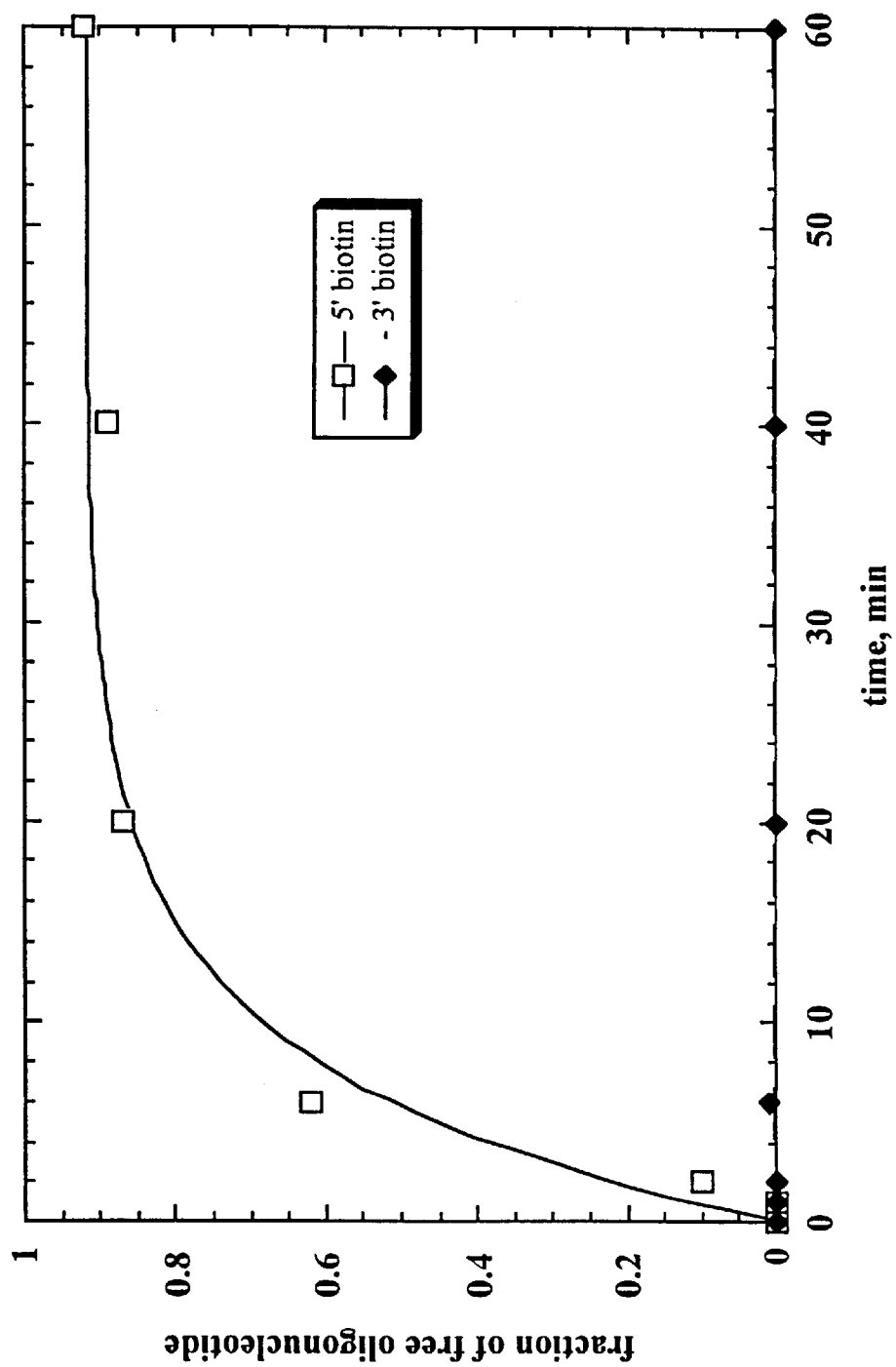
FIG. 2 shows the removal of streptavidin from a 60 mer biotin labeled oligonucleotide catalyzed by the SV40 Large T antigen. Biotin was placed on the 5' or 3' end of a 62-mer oligonucleotide. Streptavidin was bound to the oligonucleotide (10 nM) followed by incubation with the SV40 Tag helicase (4 $\mu$M). In the presence of ATP and MgCL$_2$, SV40 Tag displaced the streptavidin from the 5'-biotin labeled 62-mer (open squares) but not from the 3'-biotin labeled 62-mer. This result is consistent with 3'-to-5' unidirectional translocation of SV40 Tag on ssDNA.

Full length NS3 helicase encoded by the Hepatitis C virus is capable of displacing streptavidin from oligonucleotides (FIG. 1). It was found that full length NS3 helicase displaced streptavidin from the 5'-end, not the 3'-end, of oligonucleotides. The rate of enhancement for streptavidin displacement is more than 100-fold greater than the spontaneous dissociation rate. The SV40 large T antigen is capable of displacing streptavidin from the biotinylated oligonucleotides (FIG. 2). SV40 large T antigen also displaced streptavidin from the 5'-end, not the 3'-end, of oligonucleotides. These results, along with those described herein for Dda and gp41 helicases, support that claim that the assay is general and can be applied to any helicase.

EXAMPLE 6

The gp41 and Dda enzymes are capable of displacing streptavidin from the 3' end, but not the 5' end, of a biotinylated oligonucleotide Previous work indicated that gp41 translocates with a 5'-to-3' directional bias on ssDNA (10). Kinetic analysis of the ATPase activity of gp41 in the presence of varying length ssDNA strongly suggested that this enzyme moves primarily in one direction. Evidence is provided herein to show that Dda also translocates with a 5'-to-3' directional bias (11). The ATPase activity of Dda was measured on ssDNA substrates containing biotin-streptavidin blocks, and the resulting alteration in the ATPase kinetics on 5'-biotinylated oligonucleotides versus 3'-biotinylated oligonucleotides suggested that Dda travels with a 5'-to-3' directional bias. However, each of these approaches relied upon kinetic analyis of ATPase activity, and a more direct approach was sought for studying translocation on ssDNA.

Figure 3A:
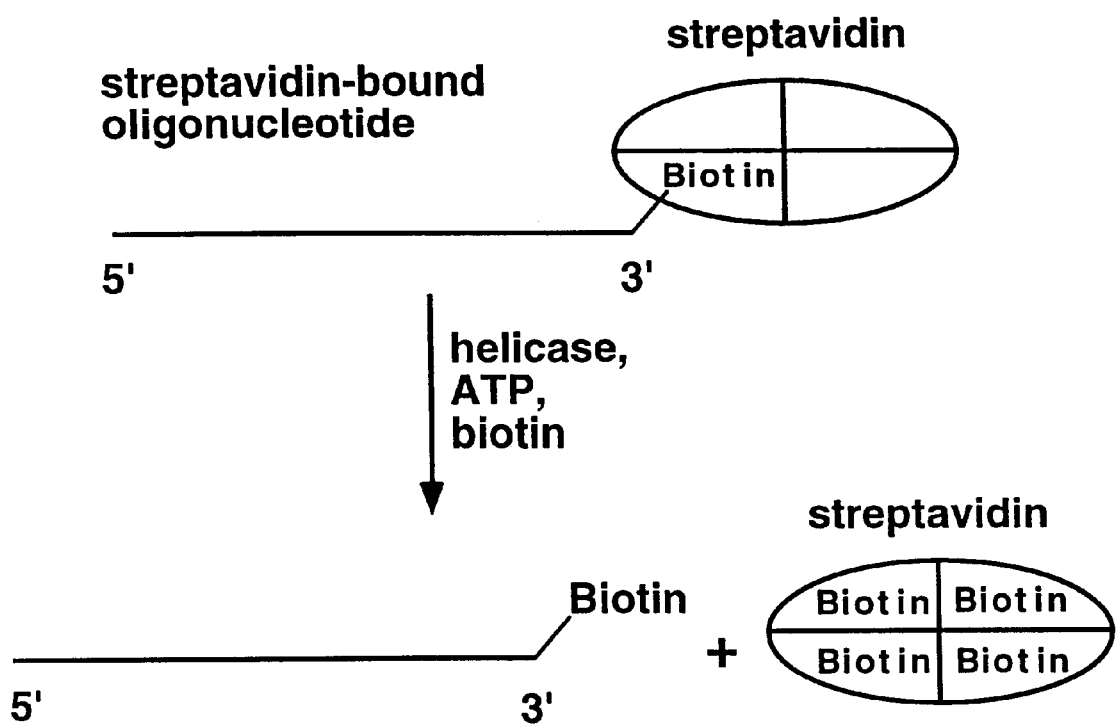
FIG. 3A illustrates the experimental protocol. Biotinylated-oligonucleotide was preincubated with ATP in Hepes (pH 7.5). After 2–3 min, free biotin trap was added, along with varying concentrations of helicase. Aliquots were removed at varying times and the helicase reaction was quenched by addition of SDS and EDTA. Any streptavidin displaced from the oligonucleotide is prevented from rebinding by free biotin. The samples were analyzed by native 15% polyacrylamide gel electrophoresis, and the quantity of streptavidin-bound oligonucleotide and free oligonucleotide was determined using a phosphorimager.
Figure 3B:
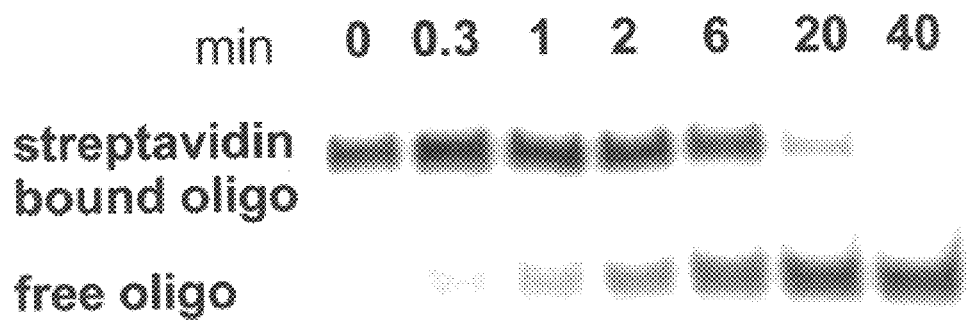
FIG. 3B shows a phosphorimage of streptavidin displacement from a 3'-biotinylated oligonucleotide.

Translocation directionality was investigated by analyzing the ability of each helicase to displace streptavidin from biotinylated oligonucleotides. A gel mobility shift assay was utilized to separate biotinylated-oligonucleotides bound by streptavidin from free biotinylated oligonucleotides (FIG. 3A). Prior to addition of helicase, the majority of 3' biotinylated 62-mer is shifted due to binding of streptavidin (FIG. 3B). After addition of 2 $\mu$M gp41 and ATP, this shift disappears over the time course of the experiment. After 40 min, virtually all of the 62-mer runs free of streptavidin on the gel. This suggests that gp41 activity on ssDNA is capable of producing a force great enough to disrupt the interaction between streptavidin and biotin. SDS (0.3% final concentration) and poly dT were included in the quencher to prevent a complicating gel shift arising from binding of gp41 to the oligonucleotide.

Several control experiments were performed to ensure that streptavidin dissociation was due to helicase activity rather than a contaminating nuclease. The presence of contaminating nuclease activity could remove the biotinylated region of the oligonucleotide, leading to the observed loss of band shifting. In one control, the displacement experiment was performed in the absence of ATP, resulting in formation of no free 62-mer throughout the 80 min time course of the experiment, suggesting that streptavidin was not removed in the absence of actively translocating gp41. In the second control, the displacement experiment was performed in the absence of excess biotin trap. If gp41 displaces streptavidin in the absence of free biotin, the streptavidin should re-bind to the oligonucleotide, and no loss of band shifting will be observed. This was indeed the case, suggesting that any loss of band shifting in the displacement experiments is due to gp41 activity, not degradation of the oligonucleotide.

Figure 3C:
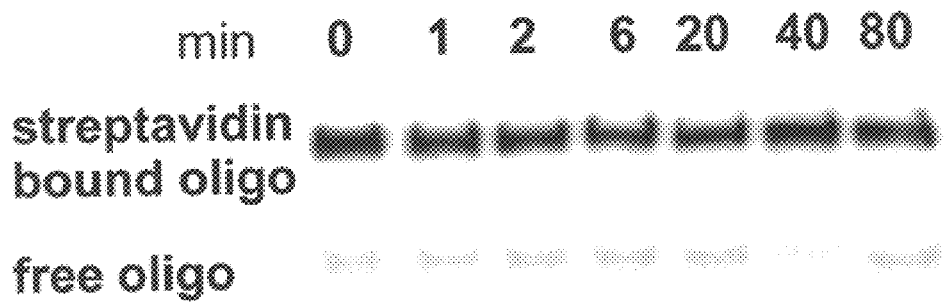
FIG. 3C shows a phosporimage of streptavidin displacement from a 5'-biotinylated oligonucleotide.

FIG. 3C shows results of the displacement experiment in the presence of the 5'-biotinylated 60-mer. Prior to gp41 addition, the majority of the oligonucleotide is shifted due to streptavidin binding. Addition of 2 $\mu$M gp41 and ATP causes no loss of band shifting, even over a period of 80 min. Thus, while gp41 activity is capable of dislodging streptavidin from the 3'-end of an oligonucleotide, it cannot dislodge it from the 5' end. Although this does not prove unidirectional translocation, it is consistent with the idea of helicases moving primarily in a 5' to 3, direction.

Figure 4:
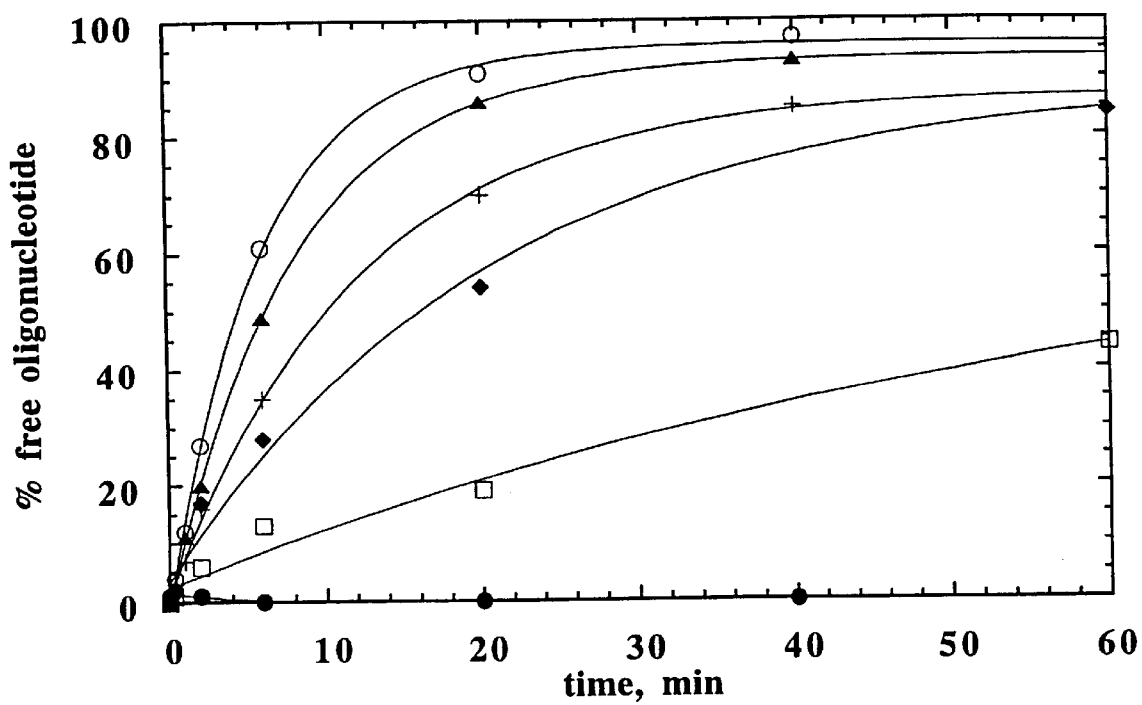
FIG. 4 shows streptavidin displacement from a 3'-biotinylated, 62-mer oligonucleotide at varying concentrations of gp41. Displacement rates were determined by fitting the data to a single exponential using the program Kaleidagraph. Displacement from 3'-biotinylated oligonucleotide: (○) 4 $\mu$M gp41, (▲) 2 $\mu$M gp41, (+) 1.5 $\mu$M gp41, (♦) 1 $\mu$M gp41, (◇) 500 nM gp41, (□) 250 nM gp41. Displacement from the 5' biotinylated oligonucleotide: (●) 4 $\mu$M gp41. Rate constants are listed in Table 1.

The results for streptavidin displacement at increasing helicase concentration are plotted in FIG. 4. The rate of displacement of streptavidin increased with increasing gp41 even at the highest helicase concentration. The solubility limit for gp41 is ~8 $\mu$M under the conditions used here. The highest final concentration of gp41 tested was 4 $\mu$m, and the rate of displacement of streptavidin still did not appear to be saturating with respect to gp41 concentration (Table 1$b$). The fastest rate of displacement measured for gp41 was 0.17 min$^{-1}$, which is ~500-fold faster than the spontaneous dissociation rate of streptavidin from biotin, 3.3×10$^{-4}$ min$^{-1}$ (26).

Figure 5:
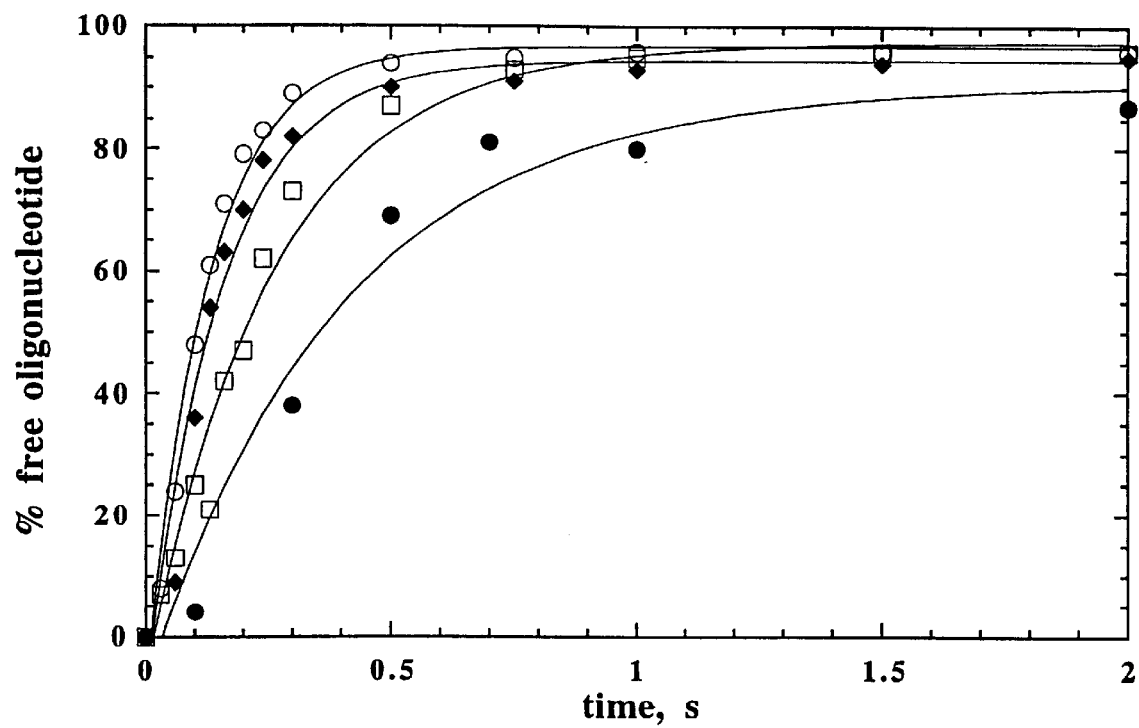
FIG. 5 shows the Dda-catalyzed displacement of streptavidin from a 3'-biotinylated, 62-mer oligonucleotide at varying helicase concentrations and mixing conditions. The lines through the data represent the best fit to a single exponential using the program Kaleidagraph. The reaction was initiated by mixing 0.25 $\mu$M Dda with the oligonucleotide and ATP (●). Alternatively, 0.25 $\mu$M Dda was preincubated with the oligonucleotide, followed by rapid mixing with ATP, which provided faster displacement rates (□). Similar rates were obtained at 1 $\mu$M Dda (○) and 2 $\mu$M Dda (♦) Rate constants are listed in Table 1.

Data for streptavidin displacement by the Dda helicase are shown in FIG. 5. Dda was much more effective than gp41 at displacing the 3'-streptavidin, although the 5'-streptavidin was not displaced, just as with gp41. Measurement of the rate of streptavidin displacement by Dda required use of a rapid mixing instrument (Kintek RQ3, Kintek, Inc.). Two conditions for initiating the reaction were examined. Dda was rapidly mixed with the oligonucleotide and ATP in one case, while in the other case, Dda was preincubated with the oligonucleotide, followed by rapid mixing with ATP. Results shown in FIG. 5 show that the fastest rates were obtained when the enzyme and DNA were preincubated.

Rates of displacement of streptavidin were measured at varying concentrations of Dda in the presence of 10 nM oligonucleotide. The rate of displacement at 1 $\mu$M enzyme was similar to that measured at 2 $\mu$M, suggesting that saturating conditions were obtained with respect to Dda (Table 1). The rate of displacement of streptavidin from the 3' end of the 62-mer was 7.9 s$^{-1}$, which is over one million-fold faster than the spontaneous dissociation rate (26).

TABLE 1

Rates of Dissociation of Streptavidin from 3'-Biotinylated 62-mer Oligonucleotide[a]

| Enzyme concentration | Dda k (s$^{-1}$) | gp41 k (min$^{-1}$) |
|---|---|---|
| 0.25 | 3.9 (2.5)[b] | 0.03 |
| 0.5 | N.D.[c] | 0.05 |
| 1.0 | 7.9 | 0.08 |
| 2.0 | 6.5 | 0.13 |
| 4.0 | N.D. | 0.17 |

[a]Rates were determined as described in FIGS. 5 and 6. The error in fitting of the data was typically + 0.5 s$^{-1}$ for rates pertaining to Dda and ±0.01 min$^{-1}$ for rates pertaining to gp41.
[b]Result obtained by initiating reaction by rapid mixing of Dda with the biotin-labeled oligonucleotide. All other rates pertaining to Dda were obtained by preincubating Dda with the biotin-labeled oligonucleotide followed by rapid mixing with ATP. Rate constants determined for gp41 were independent on the order of mixing of reagents.
[c]not determined.

EXAMPLE 7

Figure 6A:
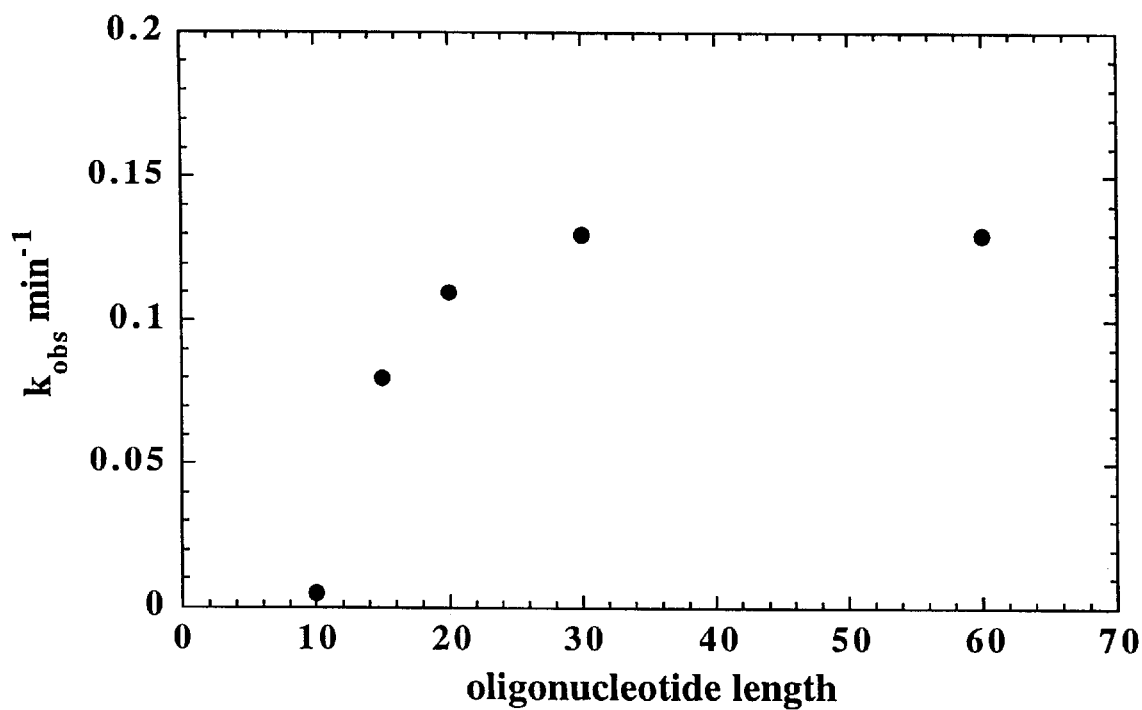
FIG. 6A: displacement rates in the presence of 2 $\mu$M gp41 are plotted versus oligonucleotide lengths of 11, 21, 30, and 62 nucleotides.

Displacement of streptavidin from biotin-labeled oligonucleotides of varying length Streptavidin displacement assays were performed with a series of 3'-biotinylated oligonucleotides of varying lengths (FIG. 6A). The rate of streptavidin displacement by gp41 (2 $\mu$M) was similar for the 62-mer, 30-mer, and 21-mer oligonucleotides. There was a decrease in the rate of displacement for the 16-mer, and a very sharp decrease in the rate of displacement for the 11-mer, suggesting that approximately 20–30 nucleotides are optimal for gp41 binding and translocation. This number of nucleotides corresponds to the number estimated to be bound by gp41 from previous gel shift experiments (10), and is similar to the 29 nucleotides that are sequestered upon binding of gene 4 helicase to ssDNA (23).

Figure 6B:
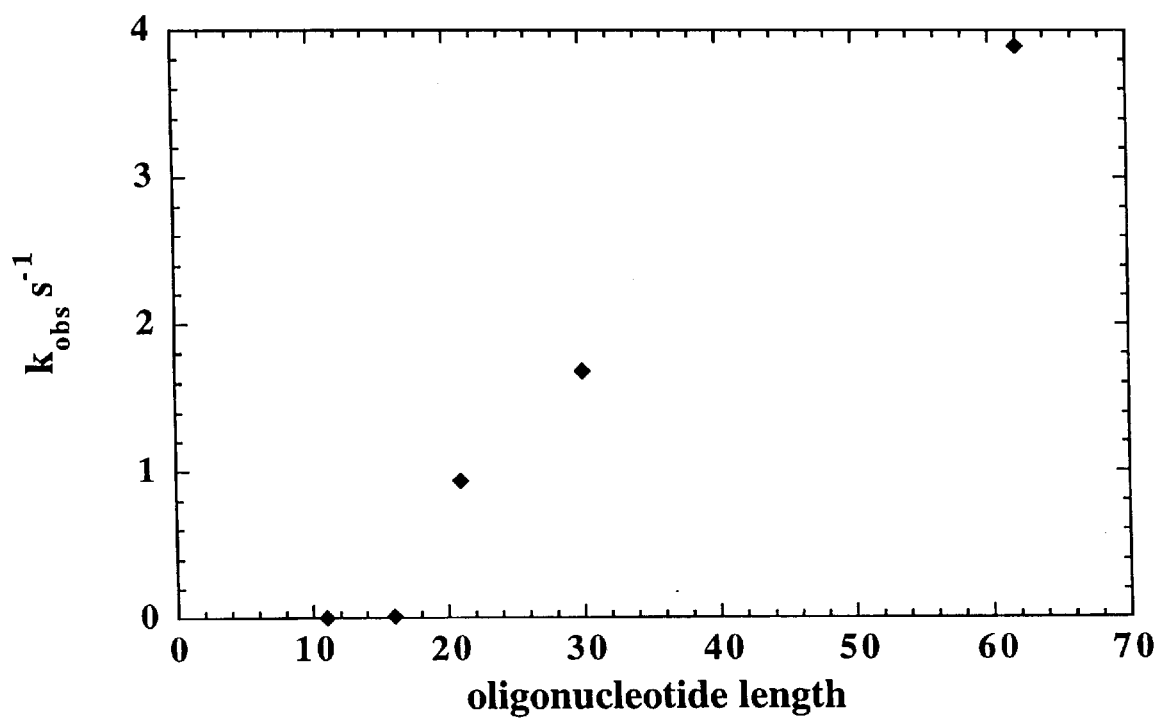
FIG. 6B: Displacement rates in the presence of 0.25 $\mu$M Dda versus oligonucleotide length.

Displacement of streptavidin from varying length oligonucleotides by Dda follows a different patten than gp41. The rate of displacement is fastest with the 62-mer, and decreases somewhat linearly with the 30-mer and 21-mer oligos. The rate decreases sharply when comparing the 21-mer to the 16-mer, and very little displacement is observed for the 11-mer (FIG. 6B). The faster rates for Dda with longer oligonucleotides may represent the need for Dda to oligomerize along the DNA in order to exhibit maximal activity, although the oligomeric form of this helicase has not been defined. Dda is known to dissociate rapidly from DNA (27, 28), and therefore may function in a different manner than gp41, which is known to exhibit high processivity (29). Further studies of Dda's possible oligomeric nature and its binding site-size will be necessary to fully explain the results in FIG. 6B.

EXAMPLE 8

Helicases can impart a force on proteins in their path

Results from previous DNA unwinding experiments in which a streptavidin block was placed on either strand of a fork substrate are slightly different for the gene 4 helicase than for the gp41 helicase. While the block on the 5'-to-3' strand was able to completely inhibit unwinding by gene 4, the block only reduced unwinding by the gp41 helicase by 8-fold (13, 32). Either gp41 was able to bypass the streptavidin block, or the streptavidin was being displaced from the biotin. The latter possibility was initially considered unlikely due to the strong interaction between biotin and streptavidin, which have a dissociation constant of ~$10^{-14}$ $M^{-1}$ (26). More importantly, the disruption force required to remove streptavidin from biotin was measured using atomic force microscopy and found to be ~250 pN (33, 34). For comparison, the force that can be generated by a molecular motor enzyme such as kinesin has been determined to be 5–10 pN (35, 36), while the largest force that has thus far been measured for any enzyme that translocates on DNA is for RNA polymerase and is 14 pN (37). The disruption force measured for removal of steptavidin from biotin is much larger than previously measured for any translocating enzyme. Therefore, in light of the result from the unwinding experiments in which gp41 unwound dupex DNA despite the streptavidin block, it was investigated whether the activity of a helicase on ssDNA could cause disruption of the streptavidin-biotin bond.

Using a gel shift assay that separates biotin-labeled oligonucleotides bound to streptavidin from those that are not, it was determined that the two helicases studied herein can rapidly displace streptavidin. At the highest protein concentration used, gp41 was capable of displacing streptavidin from biotin with a dissociation rate ~500-fold faster than the spontaneous dissociation rate of biotin from streptavidin (Table 1) (26). The reaction was dependent on the presence of ATP and the presence of excess free biotin, indicating that the displacement of streptavidin was indeed due to helicase activity. Dda was capable of displacing streptavidin at even faster rates, resulting in greater than a one million-fold enhancement in streptavidin displacement from biotin when compared to the spontaneous dissociation rate (Table 1).

These results indicate that gp41 and Dda can impart a significant force upon proteins blocking their path on ssDNA. The directional bias of the force was shown in experiments in which the biotin label was placed on the 5'-end of oligonucleotides. Neither Dda nor gp41 was able to displace any of the 5'-streptavidin under conditions in which all of the 3'-streptavidin label was rapidly removed (FIG. 3). Hence, the results are consistent with the idea that these helicases translocate unidirectionally in a 5' to 3' manner, as has been reported (10, 11). The oligomeric nature of Dda has not been defined, therefore the mode of unwinding for this enzyme remains to be determined. gp41 functions as a hexamer, with only one strand of the DNA duplex passing through the central channel. The role of force production may serve to separate the two strands, with the protein acting as a wedge and the displaced strand passing on the outside of the hexamer. With regard to models for helicase function, the production of force with a directional bias suggests that the enzyme may actively participate in the melting of duplex DNA due to translocation on ssDNA, perhaps by enhancing formation of ssDNA that already exists naturally due to thermal fluctuations at the ss/ds DNA junction (38).

Whether the displaced DNA strand interacts with gp41 in a formal manner remains to be determined, although in previous experiments, placement of a streptavidin block on the displaced strand did not impede progress of the enzyme (13). Inconsistent data regarding the interaction of the displaced strand with the gene 4 helicase has been reported. Benzo[a]pyrene-DNA adducts inhibited gene 4 helicase in a strand specific manner, suggesting a significant difference between interactions of the helicase and the two DNA strands (39). Hacker and Johnson (32) reported that little interaction with the displaced strand is necessary for the unwinding reaction to occur. These authors suggested that the displaced strand need simply be excluded from the central channel of the hexamer in order for unwinding to proceed. This is supported by an experiment in which unwinding was observed for a substrate that did not contain a 3'-tail. A streptavidin block was placed on the 3' end of the displaced strand, which excluded the strand from the central channel of the gene 4 helicase. Ahnert and Patel (40) have reported results in which the 3'-tail of the displaced strand was required, based on the observation of reduced unwinding when the 3'-ssDNA tail was converted to a dsDNA tail. The discrepancy in these results may lie in the conditions used to perform the experiments. Ahnert and Patel performed unwinding experiments at 4° C. while Hacker and Johnson performed their experiments at 10° C. or higher. The higher temperature may have led to more fraying of the ss/ds DNA. Thus, the role of the 3' tail in unwinding by gp41, gene 4 helicase, and other hexameric 5'-to-3' helicases remains to be resolved.

Dda displaces streptavidin much faster than gp41 (Table 1). These results correlate with results from DNA unwinding studies which indicate that Dda unwinds oligonucleotide substrates much faster than gp41 (13, 27). The rate limiting step in the displacement reaction may be different for the two helicases, and experiments are underway to determine the biochemical events that give rise to the difference in streptavidin displacement rates.

EXAMPLE 9

Models for helicase function

An important aspect of the work described herein is that the force generated by these helicases is produced solely on ssDNA substrates. No unique structures are required, such as a ss/dsDNA junction or concomitant binding of ssDNA and dsDNA. It is tempting to speculate that the functional requirements of gp41 and Dda are satisfied with only ssDNA and may not require dsDNA during the reaction cycle. In light of the fact that only one strand of DNA passes through the central channel of gp41, DNA unwinding may be a consequence of the ability of the enzyme to translocate unidirectionally on ssDNA. A similar suggestion has been made for the helicase activity of the rho transcription termination factor (41). Rho transcription termination factor may produce a strong force in the direction of translocation based on its ability to displace RNA polymerase from a growing transcript (41).

The fact that gp41 and Dda can cause displacement of streptavidin from biotin argues favorably for these enzymes being capable of displacing a complementary strand of DNA due to translocation. Such a mechanism could be accommodated by an inch-worm model of translocation for a monomeric or dimeric helicase, as has been proposed for the NS3 helicase of the hepatitis C virus (17). For the hexameric helicases, unidirectional translocation may be driven by rotational catalysis, based on similarities between the ATPase activity of the gene 4 helicase with the $F_1$-ATPase. The $F_1$-ATPase is known to rotate about a polypeptide subunit, which may be analogous to the possible rotation of a hexameric helicase about ssDNA (16). Some form of "subunit switching", in which one subunit of the enzyme moves relative to a second subunit which remains bound to DNA, may be responsible for translocation as has been suggested for the dimeric Rep helicase (1). Mechanisms involving unidirectional translocation on ssDNA have been characterized as "passive", although the results described here suggest that helicases can, in fact, impart a strong force on objects in their path, which would likely include complementary strands of DNA.

EXAMPLE 10
Production of force by gp41 and Dda to dislodge streptavidin from biotin If the streptavidin-biotin bond were treated as a static system, then the force required to displace streptavidin would need to be greater than the measured disruption force. However, non-covalent bonds are reversible, meaning that, ultimately, no force is required to separate the molecules (42). Fluctuations in the free energy minimum of the streptavidin-biotin bond, produced by thermal vibrations, will eventually cause the bond to break. Application of a force, even a weak one, will reduce the lifetime of the bond by diminishing the free energy minimum to an extent which may be proportional to the exerted force (42, 43, 44). Thus, gp41 and Dda need not apply a force that is equal to the measured disruption force of the streptavidin-biotin bond in order t o significantly enhance the dissociation rate of streptavidin from biotin.

The thermodynamic relationship between the force required to break the biotin-streptavidin bond has been found to correlate with the activation enthalpy rather than the overall free energy of the bond (34). The theoretical relationship between the kinetics of dissociation for a protein-protein or protein-ligand interface as a function of applied force has been reported to be logarithimic (42, 44, 45). The possibility exists that the interaction between the helicases and streptavidin causes some distortion in the streptavidin that lowers its affinity for biotin, which would complicate any attempt to relate the dissociation rates described here with the apparent force imparted by the helicase. If such a relationship can be established, then the method described here may be a simple way in which to estimate the force produced by enzymes that translocate on DNA. Others have confirmed the results herein regarding gp41's ability to dislodge streptavidin from biotin-labeled oligonucleotides.

The following references were cited herein:
1. Bird, L. E., et al. (1998) *Curr. Op. Struct. Biol.* 8, 14–18.
2. Lohman, et al. (1996) *Annu. Rev. Biochem.*, 65, 169–214.
3. Egelman, E. (1996) *Curr. Biol.* 4, 759–762.
4. West, S. C. (1996) *Cell* 86, 177–180.
5. Lohman, T. M., et al. (1998) *Cell* 93, 9–12.
6. Ellis, N. A., et al. (1995) *Cell* 83, 655–666.
7. Friedberg, E. C. (1992) *Cell* 71, 887–889.
8. Matson, S. W. (1986) *J. Biol. Chem.* 261, 10169–10175.
9. Geiselmann, J., et al. (1993) *Proc. Natl. Acad. Sci. USA* 90, 7754–7758.
10. Young, M. C., et al. (1994) *J. Mol. Biol.* 235, 1447–1458.
11. Raney, K. et al. (1995) *J. Biol. Chem.* 270, 22236–22242.
12. Dong, F., et al. (1995) *J. Biol. Chem.* 270, 7462–7473.
13. Raney, K., et al. (1996) *J. Biol. Chem.* 271, 14074–14081.
14. Kinosita, K. Jr., et al. (1998) *Cell* 93, 21–24.
15. Noji, H., et al. (1997) *Nature* 386, 299–302.
16. Hingorani, M., et al. (1997) *Proc. Natl. Acad. Sci. USA* 94, 5012–5017.
17. Kim, J. L., et al. (1998) *Structure* 6, 89–100.
18. Khan, S. (1997) *Annu. Rev. Biochem.* 66, 785–805.
19. Bensimon, D. (1996) *Structure* 4, 885–889.
20. Hacker, K. et al. (1992) *J. Biol. Chem.* 267, 20674–20681.
21. Richardson et al. (1989) *J. Biol. Chem.* 264, 4725–4731.
22. Barry, et al. (1994) *J. Biol. Chem.* 269, 33049–33062.
23. Egelman, et al. (1995) *Proc. Natl. Acad. Sci. USA* 92, 3869–3873.
24. Stasiak, A., et al. (1994) *Proc. Natl. Acad. Sci. USA* 91, 7618–7622.
25. Dean, F., et al. (1992) *J. Biol. Chem.* 267, 14129–14137.
26. Chilkoti, et al. (1995) *J. Am. Chem. Soc.* 117, 10622–10628.
27. Raney, et al. (1994) *Proc. Natl. Acad. Sci. USA* 91, 6644–6648.
28. Jongeneel et al. (1984) *J. Biol. Chem.* 259, 12925–12932.
29. Dong et al. (1996) *Proc. Natl. Acad. Sci.* 93, 14456–14461.
30. Bujalowski et al. (1994) *J. Biol. Chem.* 269, 31350–31358.
31. Yu, X., et al. (1996) *Nat. Struct. Biol.* 3, 740–743.
32. Hacker, et al. (1997) *Biochemistry* 36, 14080–14087.
33. Moy, V. T., et al. (1994) *Science* 266, 257–259.
34. Chilkoti, A., et al. (1995) *Biophys. J.* 69, 2125–2130.
35. Coppin, C. M., et al. (1995) *Biophys. J.* 68, 242s–244s.
36. Svoboda, K., et al. (1993) *Nature* 365, 721–727.
37. Yin, H., et al. (1995) *Science* 270, 1653–1656.
38. Chen, et al. (1992) *J. Biomol. Struct. Dyn.* 10, 415–427.
39. Yong, et al. (1996) *Chem. Res. Toxicol.* 9, 179–187.
40. Ahnert, et al. (1997) *J. Biol. Chem.* 272, 32267–32273.
41. Walstrom, K. et al. (1997) *Biochemistry* 36, 7993–8004.
42. Bell, G. I. (1978) *Science* 200, 618–627.
43. Khan, et al. (1997) *Annu. Rev. Biochem.* 66, 785–805.
44. Erickson, H. (1994) *Proc. Natl. Acad. Sci. USA* 91, 10114–10118.
45. Evans, E., & Ritchie, K. (1997) *Biophys. J.* 72, 1541–1555.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of screening for compounds that inhibit or stimulate helicase enzyme activity, comprising the steps of:
   (a) combining under appropriate conditions:
      (i) a helicase enzyme capable of unidirectional translocation on an oligonucleotide, and
      (ii) a biotinylated single-stranded oligonucleotide bound to streptavidin, thereby producing helicase-associated streptavidin-biotinylated-oligonucleotide;
   (b) contacting a sample of said helicase-associated streptavidin-biotinylated-oligoiucleotide with a compound, thereby producing a compound-treated helicase-associated streptavidin-biotinylated-oligonucleotide sample; and
   (c) measuring the amount of dissociation of said biotinylated oligonucleotide from streptavidin in said compound-treated helicase-associated streptavidin-biotinylated-oligonucleotide sample and an untreated helicase-associated streptavidin-biotinylated-oligonucleotide sample, wherein less dissociation of said biotinylated oligonucleotide from said streptavidin in said compound-treated helicase-associated streptavidin-biotinylated-oligonucleotide sample than in said untreated helicase-associated streptavidin-biotinylated-oligonucleotide sample indicates the compound inhibits helicase enzyme activity, wherein greater dissociation of said biotinylated oligonucleotide from said streptavidin in said compound-treated helicase-associated streptavidin-biotinylated-oligonucleotide sample than in said untreated helicase-associated streptavidin-biotinylated-oligonucleotide sample is indicative of a compound that stimulates said helicase enzyme activity.

2. The method of claim 1, wherein said streptavidin is mutated to alter its dissociation constant from biotin.

3. The method of claim 1, wherein said streptavidin is in solution.

4. The method of claim 1, wherein said streptavidin is bound to a solid support.

5. The method of claim 1, wherein said oligonucleotide is biotinylated at its 3' end.

6. The method of claim 1, wherein said oligonucleotide is biotinylated at its 5' end.

7. The method of claim 1, wherein said oligonucleotide is biotinylated at an internal nucleotide.

8. The method of claim 1, wherein said helicase is selected from the group consisting of viral, prokaryotic, eukaryotic, and bacteriophage.

9. The method of claim 1, wherein said biotinylated oligonucleotide is also labeled with a non-biotin label, wherein said non-biotin label allows for detection and quantitation of said dissociation of said biotinylated oligonucleotide from said streptavidin.

10. The method of claim 9, wherein said non-biotin label is a radionucleotide or a fluorophore.

11. A method of releasing a streptavidin-captured, biotinylated oligonucleotide, comprising the steps of:
   (a) contacting a biotinylated oligonucleotide with a streptavidin that has normal or decreased affinity for biotin, thereby forming a streptavidin-captured biotinylated oligonucleotide;
   (b) contacting said streptavidin-captured biotinylated oligonucleotide with a helicase, wherein said helicase releases said streptavidin from said biotinylated oligonucleotide; and
   (c) collecting said biotinylated oligonucleotide released from said streptavidin.

12. The method of claim 11, wherein said streptavidin is selected from the group consisting of in solution and bound to a solid support.

* * * * *